United States Patent [19]

Müller et al.

[11] Patent Number: 5,354,827
[45] Date of Patent: Oct. 11, 1994

[54] DENTAL ADHESIVES

[75] Inventors: Michael Müller, Bergisch-Gladbach; Werner Finger, Dormagen; Wolfgang Podszun; Jens Winkel, both of Cologne, all of Fed. Rep. of Germany

[73] Assignee: Bayer Aktiengesellschaft, Leverkusen, Fed. Rep. of Germany

[21] Appl. No.: 35,550

[22] Filed: Mar. 23, 1993

Related U.S. Application Data

[63] Continuation of Ser. No. 834,428, Feb. 12, 1992, abandoned.

[30] Foreign Application Priority Data

Feb. 22, 1991 [DE] Fed. Rep. of Germany ....... 4105550

[51] Int. Cl.$^5$ .................. C08F 20/58; C08F 20/70
[52] U.S. Cl. .................... 526/304; 523/118; 524/555
[58] Field of Search ............ 523/118; 524/555; 526/304

[56] References Cited

U.S. PATENT DOCUMENTS

| | | | |
|---|---|---|---|
| 3,501,405 | 3/1970 | Willette | 252/51.5 |
| 4,039,513 | 8/1977 | Naarmann et al. | 528/426 |
| 4,323,696 | 4/1982 | Schmitz-Josten et al. | 560/220 |
| 4,879,402 | 11/1989 | Reiners et al. | 560/26 |
| 4,952,241 | 8/1990 | Reiners et al. | 106/35 |
| 4,952,614 | 8/1990 | Reiners et al. | 523/115 |
| 5,068,264 | 11/1991 | Müller et al. | 523/118 |

FOREIGN PATENT DOCUMENTS

| | | |
|---|---|---|
| 0234934 | 9/1987 | European Pat. Off. . |
| 0355562 | 2/1990 | European Pat. Off. . |
| 0394787 | 10/1990 | European Pat. Off. . |
| 2739282 | 3/1978 | Fed. Rep. of Germany ...... 523/118 |
| 3703080 | 2/1987 | Fed. Rep. of Germany . |
| 3828169 | 2/1990 | Fed. Rep. of Germany ...... 526/304 |
| 2301539 | 9/1976 | France ............... 528/426 |

OTHER PUBLICATIONS

Houben–Weyl, Methoden der organischen Chemie, Band E20, Seite 80ff, Georg Thieme Verlag Stuttgart 1987.

R. S. Baratz, J. Biomat. Applications, vol. 1, 1987, S 316 ff. "Present Use of Polymers in Dentistry–An Introduction".

K. Eichner, "Zahnärztliche Werkstoffe und ihre Verarbeitung", Bd. 2, S. 135 ff, Hüthig Verlag, 5. Aufl. 1985.

*Primary Examiner*—Paul R. Michl
*Assistant Examiner*—LaVonda R. DeWitt
*Attorney, Agent, or Firm*—Sprung Horn Kramer & Woods

[57] ABSTRACT

The invention relates to formulations for use as an adhesive component for treatment of tooth hard substance, a process for their preparation and their use.

7 Claims, No Drawings

DENTAL ADHESIVES

This application is a continuation now abandoned of application Ser. No. 834,428, filed Feb. 12, 1992.

The invention relates to formulations for use as an adhesive component for the treatment of tooth hard substance, a process for their preparation and their use.

Tooth hard substance is built up from tooth enamel and dentine, which differ greatly in their composition. Tooth enamel is built up largely on a mineral basis, in particular from calcium hydroxyapatite. Dentine, in contrast, consists to a considerable proportion of organic units, such as collagen and other proteins, and contains more water.

In the context of the present invention, the adhesive components are preferably used for the treatment of tooth enamel and dentine in connection with tooth repairs.

Polymeric materials which harden are used as filling materials for tooth repairs in the dental field in particular. Fillings based on acrylate are in general preferred as the polymeric materials which harden. However, these polymeric fillings have the disadvantage that they adhere poorly to the tooth hard substance. To solve this problem, to date undercuts have sometimes been made on the dentine; for this, it was necessary to remove considerable amounts of healthy dentine beyond the region attacked.

According to another method, the dentine and the enamel surface are etched slightly with acids, such as, for example, phosphoric acid, and the filling is then undertaken. Apart from the fact that the acid has an irritating action in the oral region, it also easily penetrates through the dentinal tubules into the tooth and irritates the nerve.

Suitable priming agents which are applied to the etched enamel before the filling material is applied are the customary difunctional methacrylates. These viscous oils, in particular 2,2-bis-[4'(3"-methacryloyl-2"-hydroxypropoxy)phenyl]-propane (bis-GMA), triethylene glycol dimethacrylate or simple alkanediol dimethacrylates, indeed effect bonding to the enamel, but not to the dentine. Specific dentine adhesion promoters have been developed for this purpose. They improve the bonding to the dentine but have only an inadequate action from the clinical point of view, since gaps form at the edges between the dentine and filling material, these being the cause of secondary caries and discolourations.

One of the most suitable dentine adhesives is described in German Offenlegungsschrift 3,828,169. The active formulations contain A) (meth)acrylic acid esters containing formamide groups, of the formula

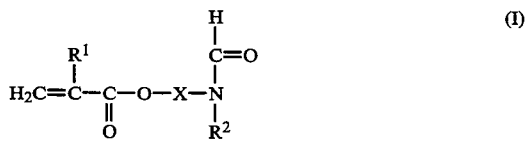

(I)

in which
R$^1$ denotes hydrogen or methyl,
R$^2$ denotes hydrogen, or alkyl (C$_1$ to C$_{12}$), aryl (C$_6$ to C$_{12}$) or aralkyl (C$_7$ to C$_{14}$) which is optionally substituted by hydroxyl, carboxyl, halogen or amino of the formula

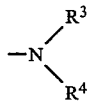

in which
R$^3$ and R$^4$ are identical or different and denote hydrogen or lower alkyl, and
X denotes a divalent aliphatic (C$_1$ to C$_{24}$) and/or cycloaliphatic (C$_5$ to C$_8$) and/or aromatic (C$_6$ to C$_{12}$) radical which can optionally be substituted by hydroxyl, carboxyl, halogen or amino of the formula

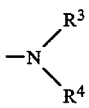

in which
R$^3$ and R$^4$ have the abovementioned meaning,
and can optionally contain one or more oxygen, sulphur and/or —NR$^3$ bridges,
wherein
R$^3$ has the abovementioned meaning,
and, if appropriate,
B) initiators, if appropriate with the addition of coactivators,
C) solvents,
D) carbonyl compounds,
E) fillers and
F) (meth)acrylic acid esters which can form crosslinkings.

In fact, it is not possible to prepare a mixture from the components A) to F) described in German Offenlegungsschrift 3,828,169 which ensures adequate bonding both to the dentine and to the tooth enamel.

The present invention was based on the object of eliminating this deficiency. For this purpose, it was not only necessary to determine preferred ranges within the wide concentration limits stated for components A) to F) in German Offenlegungsschrift 3,828,169, but a further component had to be added to achieve the object according to the invention. Surprisingly, an adequate bonding to the dentine and tooth enamel was to be achieved only after addition of an acid. This was not predictable, in particular, because acids are known to weaken the dentine by demineralisation and in this way reduce the bonding to the dentine.

Substantial advantages of the adhesives according to the invention are

The enamel and dentine are provided with the same adhesive in one working operation.

The bonding strength is significantly higher in comparison with such adhesives which have been disclosed to date.

The physiological tolerability is considerably better in comparison with adhesives known to date, in particular systems containing aldehyde.

Surprisingly, the formation of gaps at the edges can be prevented completely for the first time by using adhesives according to the invention. Thus, for example, 100% absence of gaps at the edges can be found with the formulation according to Example 1, while a gap at the edge occurs in 40% of the cases with the formulation according to Comparison Example 5.

The adhesive according to the invention for the treatment of all the tooth hard substance contains a) (meth)acrylic acid esters containing formamide groups, of the formula

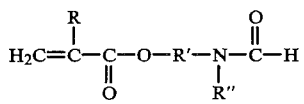  (1)

in which
R denotes hydrogen or methyl,
R' denotes a divalent aliphatic ($C_2$ to $C_5$) radical and
R'' denotes hydrogen or a monovalent alkyl radical ($C_1$ to $C_3$),
b) (meth)acrylic acid esters which can form crosslinkings,
c) solvents,
d) acids and
if appropriate
e) initiators, coactivators, fillers and dispersing agents,
and if appropriate other customary additives.

(Meth)acrylic acid esters in the context of the present invention are the esters of acrylic acid and methacrylic acid.

The substituents of the (meth)acrylic acid esters (a) containing formamide groups in the context of the general formula (1) in general have the following meaning:

A divalent aliphatic $C_2$- to $C_5$-radical represents ethylene, propylene, butylene, pentylene, 2,2 -dimethylpropylene or 1- or 2-methylbutylene. Propylene or butylene is preferred and ethylene is particularly preferred.

The monovalent radical R'' represents hydrogen or a $C_1$-, $C_2$- or $C_3$-radical, by which are meant methyl, ethyl, n-propyl or isopropyl radicals. Hydrogen or ethyl is preferred. Methyl is particularly preferred.

The following (meth)acrylic acid esters containing formamide groups may be mentioned as examples:

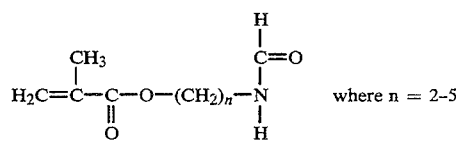  (1a)

where n = 2-5

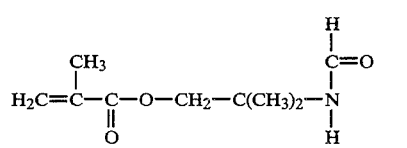  (1b)

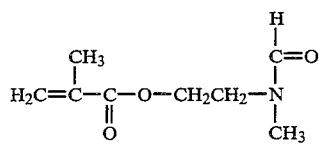  (1c)

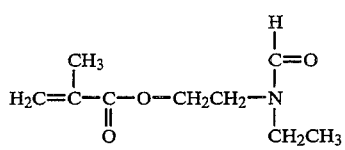  (1d)

N-Methacryloyloxyethyl-N-methylformamide (1c) is particularly preferred.

The preparation of the (meth)acrylic acid esters containing formamide groups is known per se (DE-A-1,770,964 and DE-A-2,507,189). The (meth)acrylic acid esters containing formamide groups can be prepared, for example, by reaction of alkanolamines with formic acid esters and (meth)acryloyl chloride.

The formulations according to the invention in general contain 2 to 80 parts by weight, preferably 5 to 50 parts by weight and particularly preferably 14 to 25 parts by weight of the (meth)acrylic acid esters containing formamide groups.

The compositions according to the invention can contain (meth)acrylic acid esters which can form crosslinkings. (Meth)acrylic acid esters which can form crosslinkings in general contain 2 or more polymerisable active groups in the molecule. Esters of (meth)acrylic acid with di- to pentavalent alcohols having 2 to 30 carbon atoms may be mentioned as preferred. Alkoxy(meth)acrylates and (meth)acrylates containing urethane groups are particularly preferred.

(Meth)acrylic acid esters which may be mentioned as examples are those of the formula

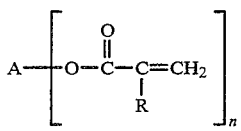

in which
A denotes a straight-chain, branched, cyclic, aliphatic, aromatic or mixed aliphatic-aromatic radical which has 2 to 25 C atoms, can be interrupted by —O— or NH bridges and can be substituted by hydroxyl, oxy, carboxyl, amino or halogen,
R denotes H or methyl and
n represents an integer from 2 to 8, preferably 2 to 4.

Compounds of the following formulae may be mentioned as preferred:

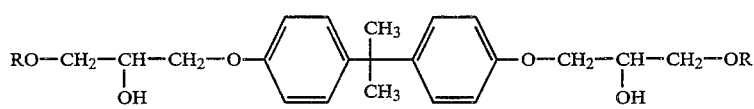

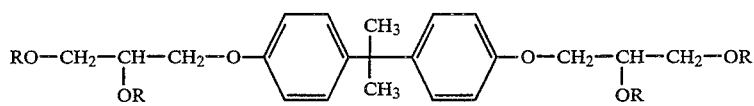

-continued
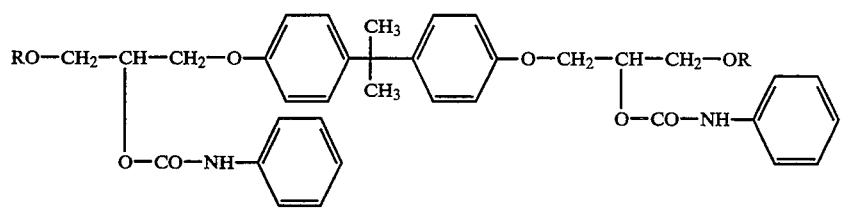
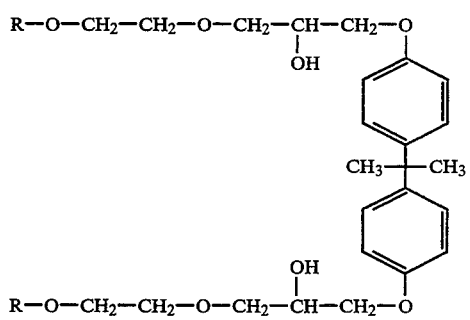
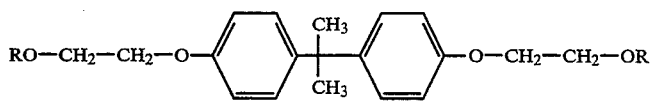
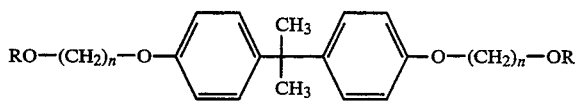
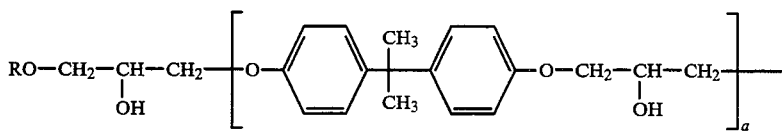
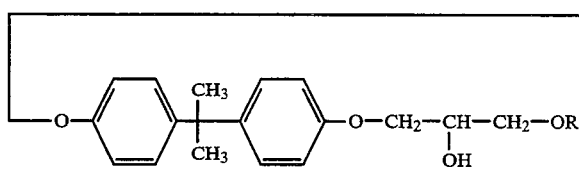
wherein a denotes a number from 1 to 4
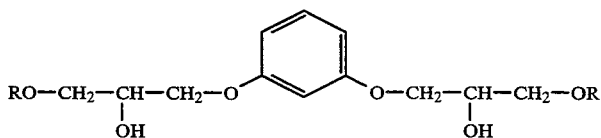
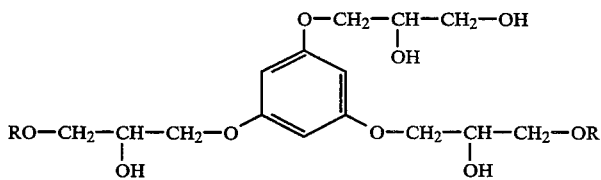
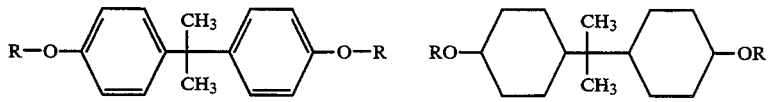

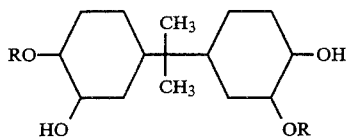
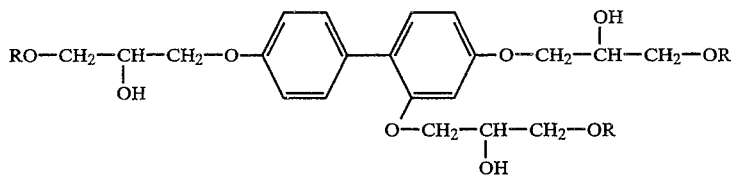
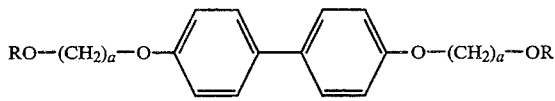
wherein a denotes a number from 1 to 4
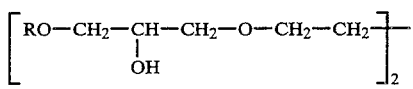
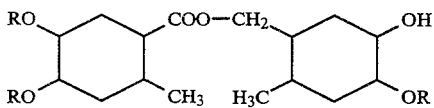
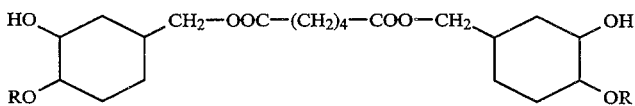
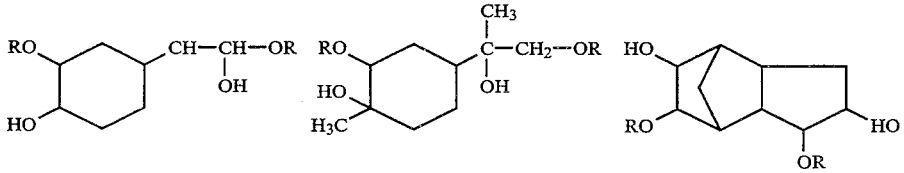
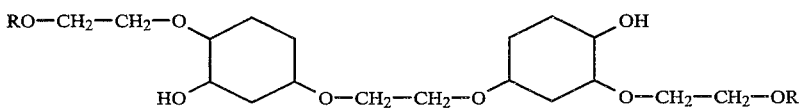
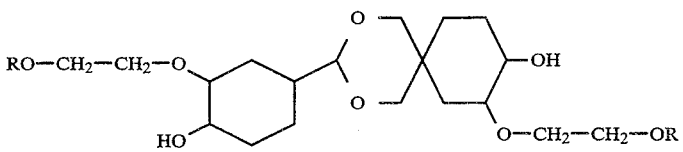
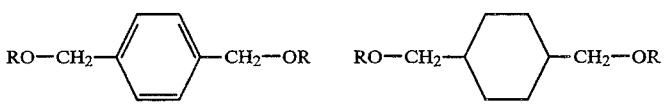
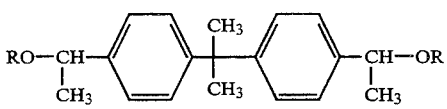

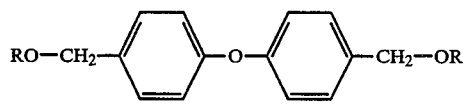
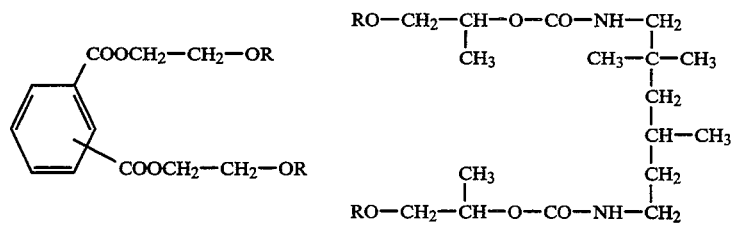
in the ortho-, meta- or para-form
yalkyl methacrylates (DE-A 3,703,120, DE-A 3,703,080
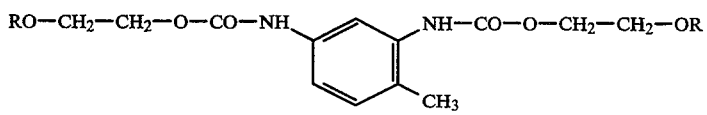
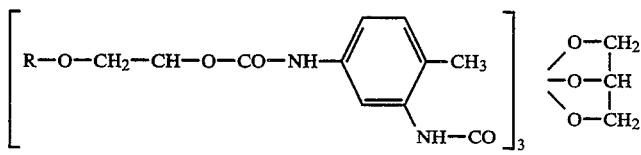
wherein R represents
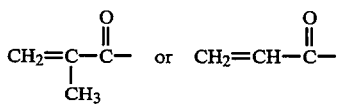
Derivatives of tricyclodecane (EP-A 0,023,686) and reaction products of polyols, diisocyanates and hydrox- and DE-A 3,703,130) may also be mentioned. The following monomers may be mentioned as examples:
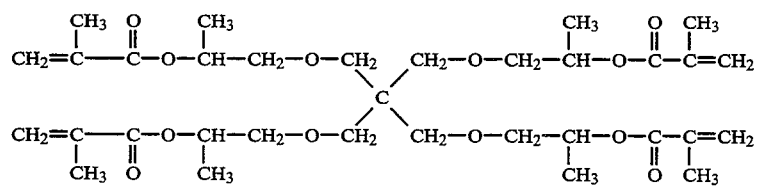
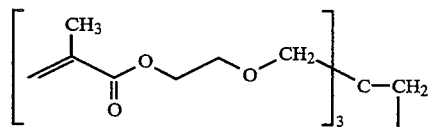
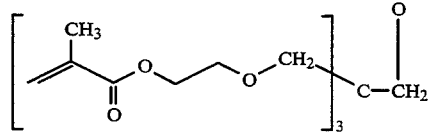
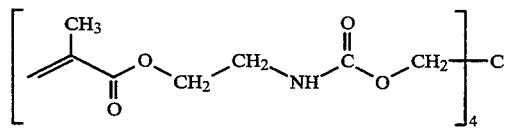

-continued
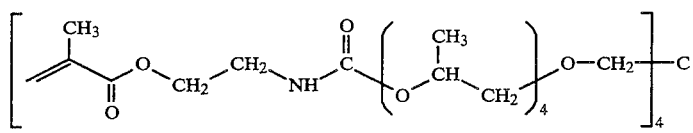
c = 1.225 (statistical mean for 4 chains)
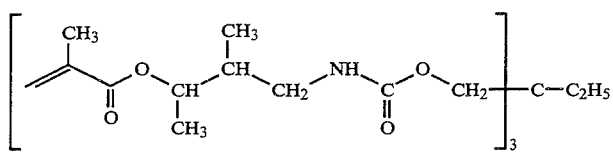
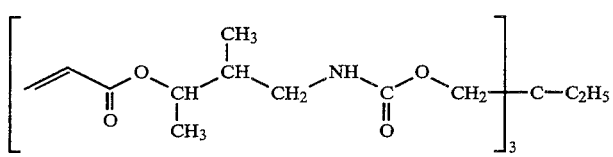
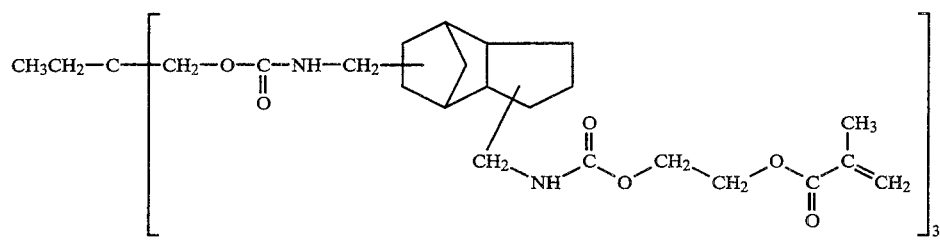
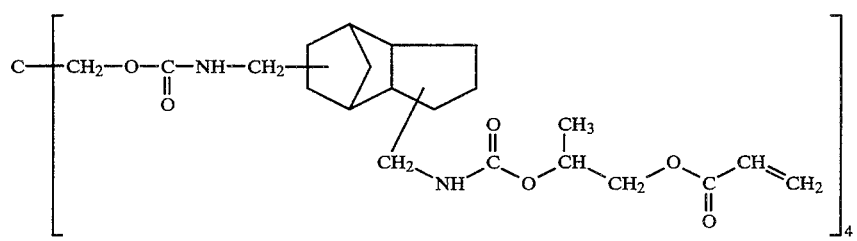
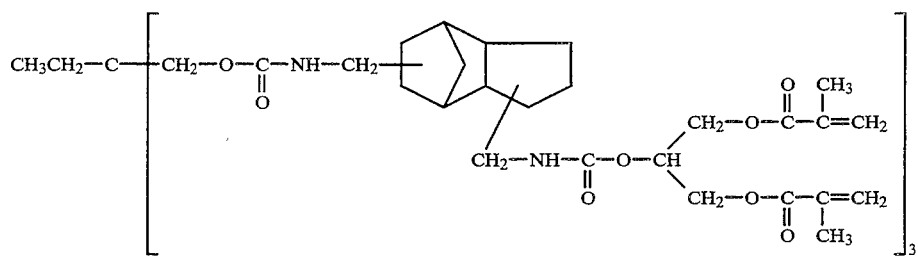
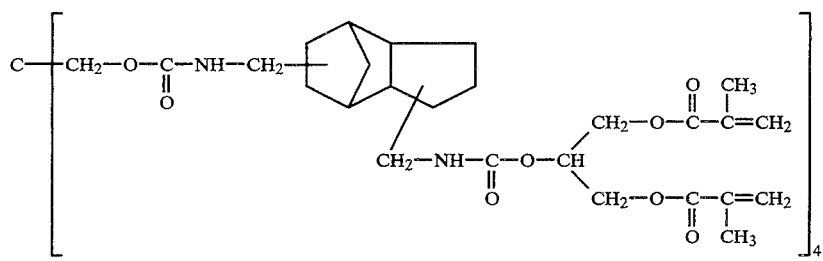

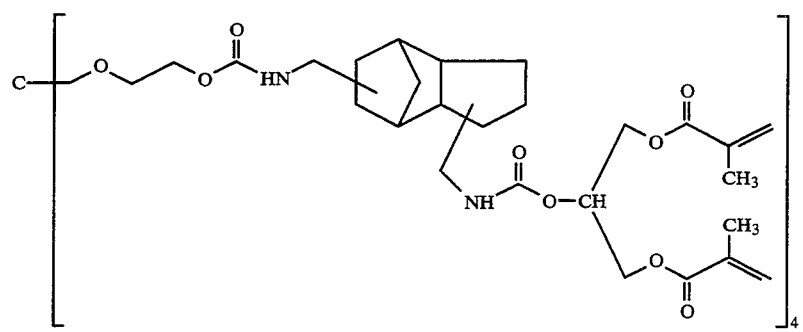
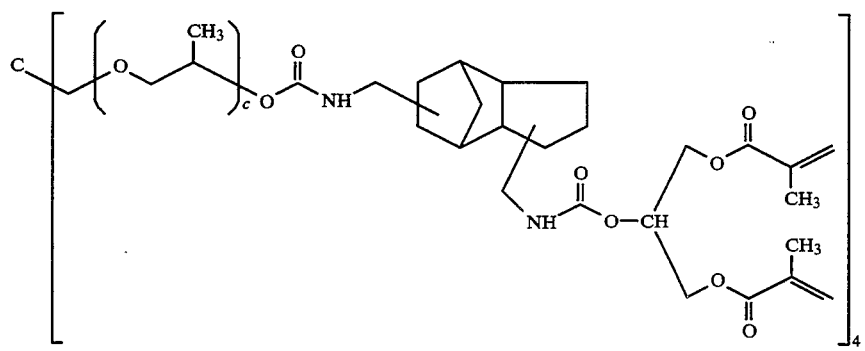
c = 1.225 (statistical mean for 4 chains)
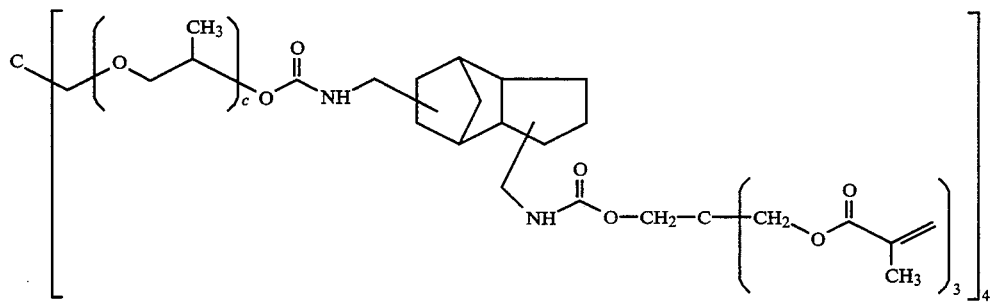
c = 1.225 (statistical mean for 4 chains)
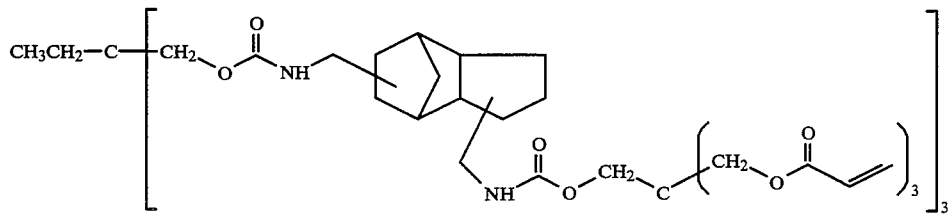
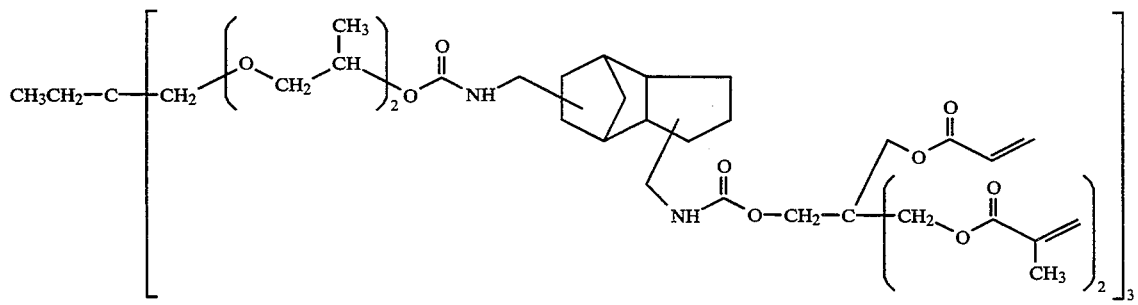

-continued
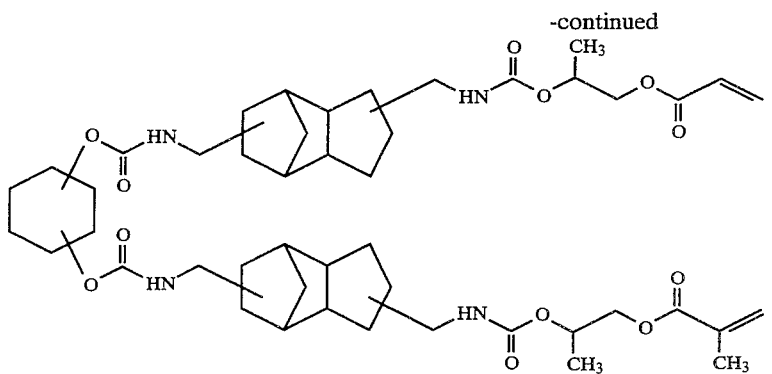
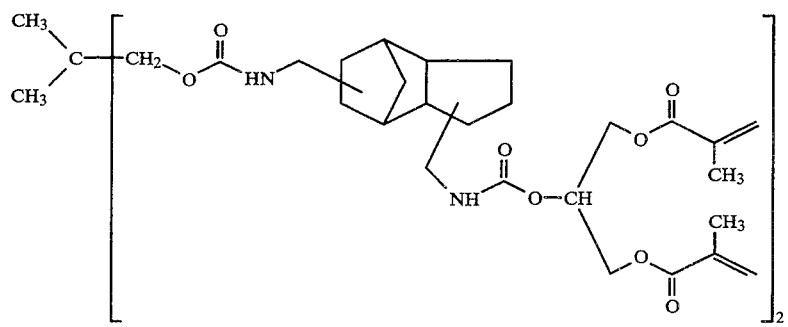
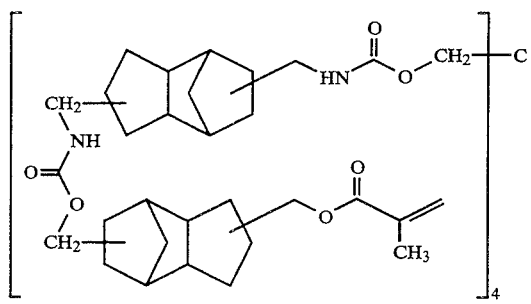
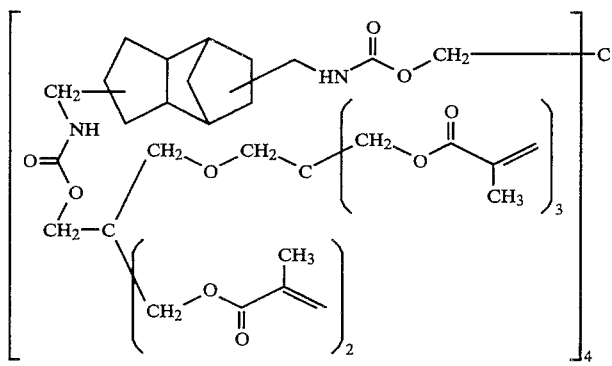
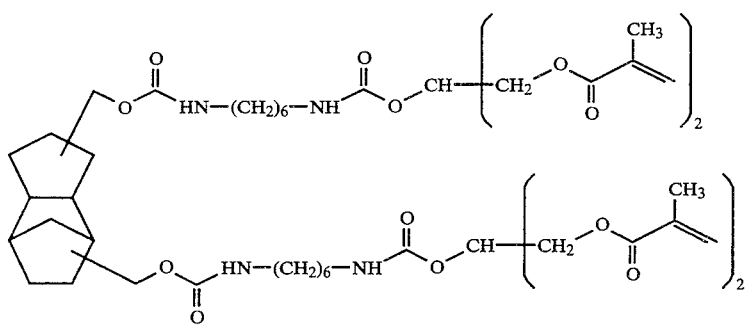

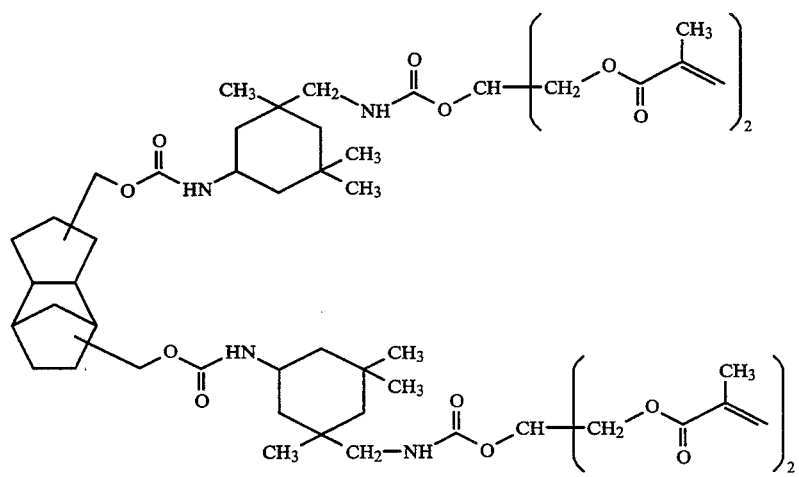
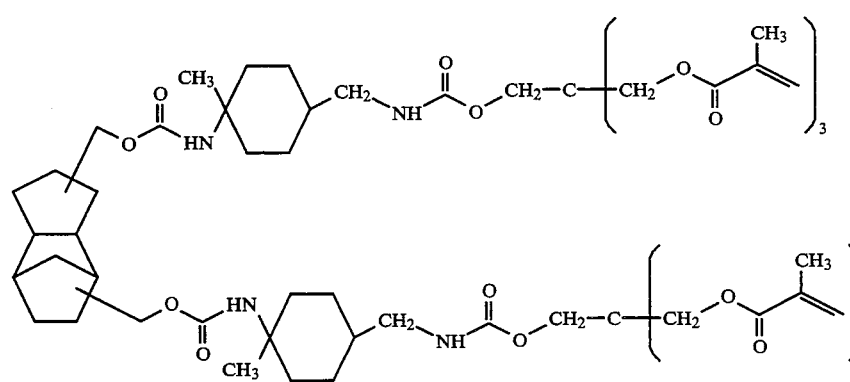
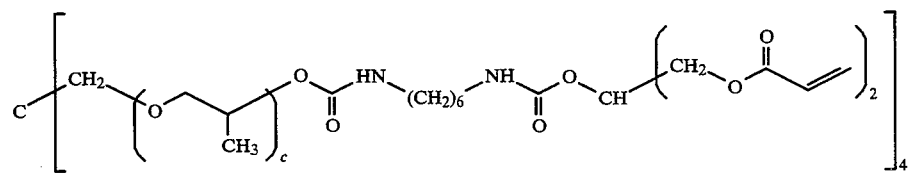
c = 1.225 (statistical mean for 4 chains)
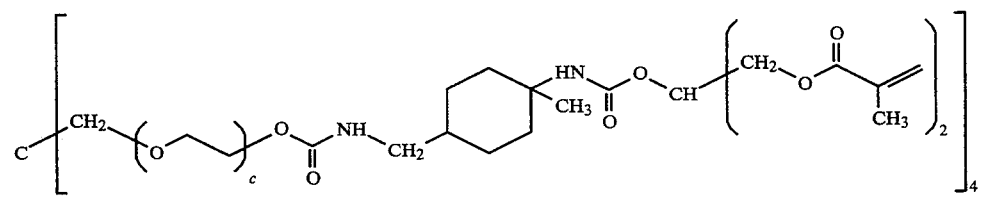
c = 1.225 (statistical mean for 4 chains)
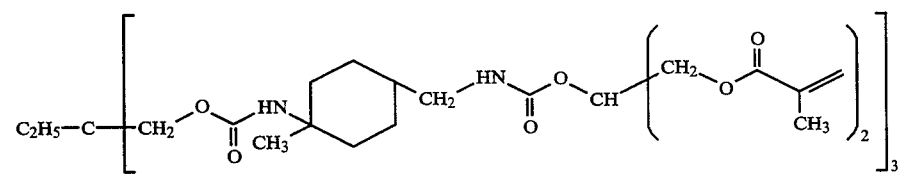

-continued

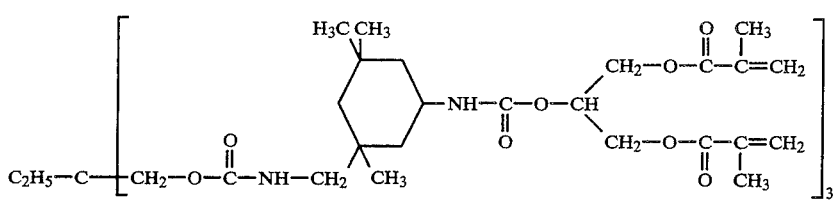

The particularly preferred methacrylic acid ester is the so-called bis-GMA of the formula

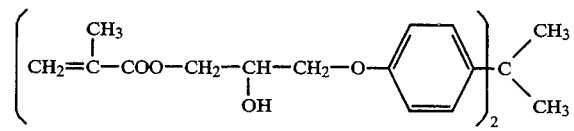

It is of course possible to employ mixtures of the various (meth)acrylic acid esters which can form cross-linkings. Mixtures of 20 to 70 parts by weight of bis-GMA and 30 to 80 parts by weight of triethylene glycol dimethacrylate may be mentioned as examples.

The formulations according to the invention in general contain 0.3 to 80 parts by weight, preferably 1 to 50 parts by weight and particularly preferably 4 to 30 parts by weight, of the methacrylic acid esters which can form crosslinkings.

The solvents in the context of the present invention should dissolve the component and should be non-toxic, because of their use. Solvents which may be mentioned as preferred are water and volatile organic solvents, such as methanol, ethanol, propanol, isopropanol, acetone, methyl ethyl ketone, methyl or ethyl acetate and tetrahydrofuran.

In general, 10 to 1000 parts by weight, preferably 30 to 300 parts by weight, particularly preferably 50 to 80 parts by weight, of the solvent are employed, based on the total mixture.

Acids which can be used in the context of the present invention are propionic, maleic, oxalic, citric, tartaric, malic, pyruvic or p-toluenesulphonic acid. Formic acid is preferred, and acetic acid is particularly preferred.

In general, 0.3 to 20, preferably 1 to 15 and particularly preferably 2 to 7 parts by weight of the acid are employed, with respect to the total mixture.

Initiators in the context of the present invention are agents which form free radicals which can trigger off a free radical polymerisation. Photoinitiators which trigger off free radical polymerisation under the action of light, for example UV light, visible light or laser light, are preferred.

The so-called photopolymerisation initiators are known per se (Houben-Weyl, Methoden der organischen Chemie (Methods of Organic Chemistry), Volume E20, page 80 et seq., Georg Thieme Verlag Stuttgart 1987). These are preferably mono- or dicarbonyl compounds, such as benzoin and derivatives thereof, in particular benzoin methyl ether, benzil and benzil derivatives, for example 4,4-oxydibenzil, and other dicarbonyl compounds, such as diacetyl, 2,3-pentanedione and α-diketo derivatives of norbornane and substituted norbornanes, metal carbonyls, such as manganese pentacarbonyl, or quinones, such as 9,10-phenanthrenequinone and naphthoquinone. Camphorquinone is particularly preferred.

The formulations according to the invention in general contain 0 to 2 parts by weight, preferably 0.1 to 0.5 part by weight, of the initiator per part by weight of the (meth)acrylic acid ester containing formamide groups. If one of the components to be joined, which is in contact with the adhesive component according to the invention, already contains an initiator of the type described, the initiator in the adhesive component can also be dispensed with completely.

It may be advantageous to add coactivators which accelerate the polymerisation reaction to the formulations according to the invention. Examples of known accelerators are amines, such as p-toluidine and dimethyl-p-toluidine, trialkylamines, such as trihexylamine, polyamines, such as N,N,N′,N′-tetraalkylalkylenediamine, barbituric acid and dialkylbarbituric acid.

The coactivators are in general employed in an amount of 0 to 4% by weight, preferably 0.2 to 1% by weight, based on the amount of polymerisable compounds.

The compositions according to the invention can contain fillers as further components. Fine powders which have a particle diameter in the range from 0.1 to 100 μm (if appropriate also in a polydisperse distribution) are the preferred fillers. Fillers can be the fillers customary in the dental field (R. S. Baratz, J. Biomat. Applications, Vol. 1, 1987, pages 316 et seq.), such as inorganic glasses, silicon dioxide powder, aluminium oxide powder or quartz powder.

Adhesive cements which are particularly suitable for fixing bridges, crowns and other veneer materials are formed by a content of fillers in the formulations according to the invention.

The content of the filler is in general 0 to 80 parts by weight, preferably 40 to 70 parts by weight, based on the total formulation.

Dispersing agents which can be employed according to the invention can be ionic or nonionic surfactants.

Examples of preferred anionic surfactants are: phosphates, such as di-(2-ethylhexyl) phosphate Na salt, alcohol sulphates, such as oleyl alcohol sulphate, alkyl($C_6$ to $C_{20}$)benzene sulphonates and alkyl($C_8$ to $C_{24}$)sulphonates, in particular sulphosuccinic acid dioctyl ester Na salt.

Preferred cationic surfactants can be, for example: quaternary ammonium salts, such as, for example, methyltrioctylammonium chloride and methyl-tricaprylylammonium chloride.

Nonionic surfactants in the form of fatty acid derivatives of polyols or of ethylene oxide, ethoxylated fatty alcohols and phenols, as well as amphoteric surfactants, such as alkylaminoethanesulphonic acid, can also be employed according to the invention. Surface-active high molecular weight compounds are particularly preferred. Compounds which may be mentioned are water-soluble polyvinyl compounds, such as polyvinyl acetate, polymethacrylic acid and polyacrylic acid and alkali metal salts thereof, and copolymers of sodium methacrylate and alkyl methacrylates. Cellulose derivatives, such as methylcellulose and carboxymethylcellulose, are furthermore particularly suitable. Poly-N-vinylpyrrolid-2-one is especially suitable.

Copolymerisable nonionic surfactants of the type of the mono-(meth)acrylates of polyalkylene oxides, it being possible for the OH-terminated molecule end also to be terminally blocked, for example, by methyl, are very particularly preferred. The following products of Nippon Oil & Fats may be mentioned as examples:

Blemmer 55 PET-800:
$H_2C=CCH_3—CO—O—(EO/THF)_n—H$ where M:700–880 g/mol,

Blemmer 50 PMEP-800 B:
$H_2C=CCH_3—CO—O—(PO)_m(EO)_n—CH_3$ where M:800–900 g/mol wherein EO represents ethylene oxide, THF represents tetrahydrofuran and PO represents propylene oxide.

In general, 0 to 10 parts by weight, preferably 0.1 to 5 parts by weight and particularly preferably 0.3 to 2 parts by weight, of dispersing agents are employed.

The adhesive components according to this invention can furthermore contain up to 10 parts by weight of customary additives, such as stabilisers, inhibitors, light stabilisers, dyestuffs, pigments or fluorescent substances.

The formulations according to the invention can be prepared by mixing all the components a) to d) or a) to e) by vigorous stirring.

The formulations according to the invention can be used as an adhesive component for the simultaneous treatment of tooth enamel and dentine. However, treatment of the dentine by itself with this component is also simplified compared with German Offenlegungsschrift 3,828,169, since the working step needed in that specification of application of a sealing material (compare Example 12 of German Offenlegungsschrift 3,828,169) can be spared according to the present invention.

In a particular embodiment, the tooth enamel and dentine are conditioned together with a liquid having a pH in the range from 0.1 to 3.5 before the treatment with the formulation according to the invention.

This liquid in general contains acids having a $pK_a$ value of less than 5 and if appropriate an amphoteric amino compound having a $pK_a$ value in the range from 9.0 to 10.6 and a $pK_B$ value in the range from 11.5 to 12.5. The conditioning liquid can contain, for example, the following acids:
phosphoric acid, nitric acid, pyruvic acid, citric acid, oxalic acid, ethylenediaminetetraacetic acid, acetic acid, tartaric acid, malic acid or maleic acid.

Amphoteric amino compounds which may be mentioned are, preferably, compounds of the formula $$R^2—\underset{\underset{R^3—NH}{|}}{\overset{\overset{H}{|}}{C}}—R^1$$

in which
$R^1$ represents a carboxyl group,
$R^2$ denotes hydrogen or a lower alkyl radical which is optionally substituted by hydroxyl, thio, methylthio, carboxyl, amino, phenyl, hydroxy-phenyl or the groups

[indol-3-yl structure], [guanidino group $H_2N-C(=NH)-NH-$ with $H_2N$ groups]

and
$R^3$ denotes hydrogen or phenyl, and
wherein the radicals $R^1$ and $R^3$ can be linked by a propyl radical, or
in which
$R^1$ represents hydrogen,
$R^2$ represents the group

—A—NH$_3$X, in which
A represents a divalent alkylene radical having 1 to 6 carbon atoms and
X represents halogen, and
$R^3$ denotes hydrogen.

The following amphoteric amino compounds may be mentioned as examples: glycine, serine, threonine, cysteine, thyrosine, asparagine,, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride, butylenediamine hydrobromide, leucine hydrochloride and histidine hydrochloride.

The conditioning liquid can furthermore contain substances from the group comprising polyethylene glycols and metal hydroxides. In particular, the abovementioned polybasic acids can also be employed as partial metal salts, as long as free acid functions remain.

Conditioning liquids which contain at least one of the acids from the group comprising oxalic acid, ethylenediaminetetraacetic acid and citric acid and if appropriate an amphoteric amino compound from the group comprising glycine, N-phenylglycine and proline are particularly preferred.

The formulations according to the invention can be used, for example, as follows:

For a dental repair, for example, after mechanical preparation of the tooth enamel and dentine the conditioning liquid is first applied and is allowed to act for a short time (for example 60 seconds), and the tooth material is rinsed with water and dried in a stream of air. The formulation according to the invention is then applied in a thin layer, for example with a small brush, and is dried in a stream of air. After the treatment according to the invention, the actual filling composition, for example filling compositions of plastic which are customary in the dental field (K. Eichner, "Zahnärztliche Werkstoffe un ihre Verarbeitung (Dental Materials and Their Processing)", Volume 2, page 135 et seq., Hüthig Verlag, 5th Edition 1985), is applied.

The formulations according to the invention can be used in a similar manner for fixing crowns, bridges and similar aids.

EXAMPLES 1 TO 3 (PREPARATION)

The adhesive components according to the invention and the comparison components are produced by intensive mixing of the constituents listed in the following examples.

Example 1

23.4 g of N-methacryloyloxyethyl-N-methylformamide
5.6 g of bis-GMA
2.8 g of acetic acid
36.0 g of water
32.0 g of ethanol
0.06 g of camphorquinone
0.14 g of p-N,N-dimethylaminobenzenesulphonic acid N',N'-diallylamide

Example 2

23.3 g of N-methacryloyloxyethyl-N-methylformamide
5.6 g of bis-GMA
2.8 g of acetic acid
35.8 g of water
31.9 g of ethanol
0.06 g of camphorquinone
0.14 g of p-N,N-dimethylaminobenzenesulphonic acid N',N'-diallylamide
0.30 g of Blemmer PMEP-800 B

Example 3

26.6 g of N-methacryloyloxyethyl-N-methylformamide
5.6 g of bis-GMA
2.8 g of acetic acid
34.3 g of water
30.5 g of ethanol
0.06 g of camphorquinone
0.16 g of p-N,N-dimethylaminobenzenesulphonic acid N',N'-diallylamide

EXAMPLES 4 AND 5 (COMPARISON EXAMPLES)

Example 4: (corresponding to Example 8 of DE-A 3,828,169)

260 g of water
110 g of N-methacryloyloxyethyl-N-methylformamide
300 g of camphorquinone

Example 5

24.1 g of N-methacryloyloxyethyl-N-methylformamide
5.8 g of bis-GMA
37.0 g of water
32.9 g of ethanol
0.06 g of camphorquinone
0.14 g of p-N,N-dimethylaminobenzenesulphonic acid N',N'-diallylamide The conditioning solution used for the technological investigations is obtained by mixing the following constituents:

2.9 g of glycine
2.6 g of Al(NO$_3$)$_3$×9 H$_2$O
1.6 g of oxalic acid×2 H$_2$O
93.1 g of water.

Example 6: (Use test, bonding strength)

The effectiveness and suitability of the adhesives (Examples 1 to 5) is investigated by determination of the shear bonding strength on dentine and enamel. Human teeth, which were stored in 1% strength chloramine solution for a maximum of three months after extraction, are used. Before being used in the test, the teeth are cleaned thoroughly under running water and stored in physiological saline solution for at least three and not more than ten days. The day before being used in the bonding test, the teeth are embedded individually in cylindrical rubber moulds of 25 mm diameter and 12 mm height using epoxy resin (®LEKUTHERM X20, hardener T3). The teeth are ground by wet grinding on SiC paper of grain 240, 320, 400 and finally 600 until an enamel surface of adequate size or a dentine surface close to the enamel is exposed for tyeing on a cylinder of plastic of 3.5 mm diameter. After rinsing with deionised water and drying in a stream of air, the area is cleaned with the conditioning solution and a cotton-wool pellet for 30 seconds, rinsed with water and dried, before the adhesive is applied with a brush, left on the surface for 30 seconds and then dried carefully in a stream of compressed air. The sample pretreated in this way is firmly clamped in a clamping device under a divisible Teflon mould with a cylindrical receptacle 3.5 mm wide and 1 mm high. The filling material of plastic ®Pekafill (U) is then introduced into the cylindrical mould using a syringe, covered with a strip which is impermeable to O$_2$ and activated for 60 seconds under the opened emitted light opening of a ®Translux CL polymerisation lamp (Kulzer). Immediately thereafter, the sample is removed from the holder. The Teflon mould is removed and the sample is kept in warm water at 23° C. for 15 minutes until the shear stress is started, which is effected with the aid of a pressure piston parallel to and applied against the surface of the embedded tooth at an advance speed of 1 mm/minute until the components separate. The shear bonding strength, which is the quotient of the breaking force and the contact area on the tooth, is determined on in each case 5 samples and stated as the mean thereof with standard deviations.

Example 7 (Use test, tooth cavity)

To simulate the clinical use of adhesives and filling materials of plastic, cavities are prepared and filled in extracted teeth which have a previous history as in Example 6. The adaptation of the filling material to the edge of the cavity is determined as a measure of the effectiveness.

The extracted teeth are subjected to wet grinding on an undamaged approximal side on SiC paper of grain 240, 320, 400 and 600 until a dentine area of sufficient size to accommodate a cylindrical cavity about 3 mm wide is exposed. The cavity is prepared down to a depth of about 1.5 mm with the customary dental preparation diamonds of medium grain size and abundant cooling with water, and is then rinsed with water and dried. The cavity is cleaned with an impregnated cotton-wool pellet for 30 seconds as in the preceding example and is then washed out and dried before the adhesive is brushed on, left for 30 seconds and finally dried. The filling material of plastic ®Pekafill (U) is introduced into the cavity with a syringe. The excess is covered with a strip which is impermeable to O$_2$ before being activated (60 seconds) with a ®Translux CL photopolymerisation unit (Kulzer). Immediately after the polymerisation, the filled tooth is kept in warm water at 23° C. for 15 minutes. Thereafter, the excess is removed by grinding on moist SiC paper of grain 400 and 600. About 0.1 mm of the cavity height is worn away during this operation. The tooth is rinsed with water, dried in a stream of air and immediately inspected in a reflected light microscope under 500-fold magnification. The maximum width of any gap present at the edges is measured with the aid of an eyepiece screw micrometer. The average maximum gap width of in each case 5 fillings is stated as the measurement value. The microscopic examination of the individual teeth was concluded in less than 10 minutes in all cases.

It was thus ensured that the gaps at the edges measured were not formed or affected in their width by dehydration of the dentine.

The results are summarised in the following table:

| Formulation according to Example No. | Shear bonding strength [N/mm] | |
|---|---|---|
| | on enamel | on dentine |
| 1 | 9.6+/−1.1 | 7.2+/−1.1 |
| 5* | 8.7+/−1.2 | 5.6+/−1.1 |
| 2 | 14.4+/−3.3 | 8.9+/−0.1 |
| 3 | 10.7+/−1.6 | 9.9+/−2.1 |
| 4** | <2 | <2 |

*Comparison example: formulation as in Example 1 but without acetic acid.
**Comparison Example according to German Offenlegungshrift 3,828,169 observing the simplified procedure described here under Example 6 and 7.

A 100% absence of gaps at the edges was found with the formulation according to Example 1, while a gap at the edge occurs in 40% of the cases with the formulation according to Comparison Example 5.

We claim:

1. Formulations containing by weight
   a) 2–80 parts of (meth)acrylic acid esters containing formamide groups, of the formula

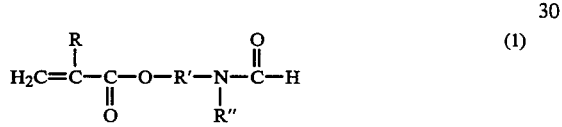 (I)

in which
R denotes hydrogen or methyl,
R' denotes a divalent aliphatic ($C_2$ to $C_5$) radical and
R" denotes hydrogen or a monovalent alkyl radical ($C_1$ to $C_3$),
   b) 0.3–80 parts of (meth)acrylic acid esters which can form crosslinkings,
   c) 10–1000 parts of solvents, and
   d) 0 to 2 parts of initiators, 0 to 4% of coactivators and 0–80% of fillers wherein
   e) 0.3–20 parts of acids and
   f) 0–10 parts of dispersing agents are added.

2. Formulations according to claim 1, characterised in that N-methacryloyloxyethyl-N-methylformamide is used as component (a).

3. Formulations according to claim 1, characterised in that of the components
   (a) 5–50 parts by weight,
   (b) 1–50 parts by weight,
   (c) 50–200 parts by weight and
   (e) 1–15 parts by weight
are employed for their preparation, the amounts stated for the components being based on the total formulation.

4. Formulations according to claim 1, characterised in that of the components
   (a) 14–25 parts by weight,
   (b) 4–30 parts by weight,
   (c) 50–100 parts by weight and
   (e) 2–7 parts by weight
are employed for their preparation, the amounts stated for the components being based on the total formulation.

5. Formulations according to claim 1, characterised in that as component
   (a) 23.4 parts by weight of N-methacryloyloxyethyl-N-methylformamide,
   (b) 5.6 parts by weight of bis-GMA,
   (c) 36 parts by weight of water and 32 parts by weight of ethanol,
   (d) 0.06 parts by weight of camphorquinone and 0.14 parts by weight of p-N,N-dimethylaminobenzenesulphonic acid N',N'-diallylamide and
   (e) 2.8 parts by weight of acetic acid
are employed for their preparation, the amounts stated for the components being based on the total formulation.

6. A method for treatment of tooth damage comprising applying the formulations according to claim 1.

7. Dental adhesives comprising formulations according to claim 1.

* * * * *